(12) United States Patent
Bush

(10) Patent No.: US 7,819,126 B2
(45) Date of Patent: Oct. 26, 2010

(54) MINIATURE DENTAL FLOSSING PACKET

(76) Inventor: Theodore K. Bush, 889 Kahena St., Honolulu, HI (US) 96825

( * ) Notice: Subject to any disclaimer, the term of this patent is extended or adjusted under 35 U.S.C. 154(b) by 464 days.

(21) Appl. No.: 12/002,697

(22) Filed: Dec. 17, 2007

(65) Prior Publication Data

US 2009/0151747 A1 Jun. 18, 2009

(51) Int. Cl.
*A61C 15/00* (2006.01)
(52) U.S. Cl. ........................ 132/323; 132/329
(58) Field of Classification Search ................ 132/321, 132/323–329; 206/63.5
See application file for complete search history.

(56) References Cited

U.S. PATENT DOCUMENTS

| 4,292,705 | A | * | 10/1981 | Stouffer | 15/110 |
| 4,519,408 | A | * | 5/1985 | Charatan | 132/321 |
| 4,579,221 | A | * | 4/1986 | Corella | 206/63.3 |
| 4,712,572 | A | * | 12/1987 | Hovel, III | 132/321 |
| 4,852,728 | A | * | 8/1989 | Court | 206/63.5 |
| 4,986,289 | A | * | 1/1991 | McWhorter | 132/323 |
| 5,014,725 | A | * | 5/1991 | Patscot et al. | 132/324 |
| 5,174,314 | A | * | 12/1992 | Charatan | 132/328 |
| 5,911,229 | A | * | 6/1999 | Chodorow | 132/323 |
| 5,915,392 | A | * | 6/1999 | Isaac | 132/200 |
| 6,234,182 | B1 | * | 5/2001 | Berglund | 132/323 |
| 6,455,083 | B1 | * | 9/2002 | Wang | 426/104 |
| 2004/0048231 | A1 | * | 3/2004 | Perlin | 434/263 |

* cited by examiner

*Primary Examiner*—Robyn Doan
(74) *Attorney, Agent, or Firm*—Peters Verny, LLP; Hana Verny

(57) ABSTRACT

A miniature dental flossing packet suitable for single use unobtrusive flossing. The miniature dental floss packet comprising a length of dental floss stored within and unremovably attached to a dental floss holder. A method for forming, fabrication and manufacturing a miniature dental floss packet.

13 Claims, 4 Drawing Sheets

Fig. 1A-D

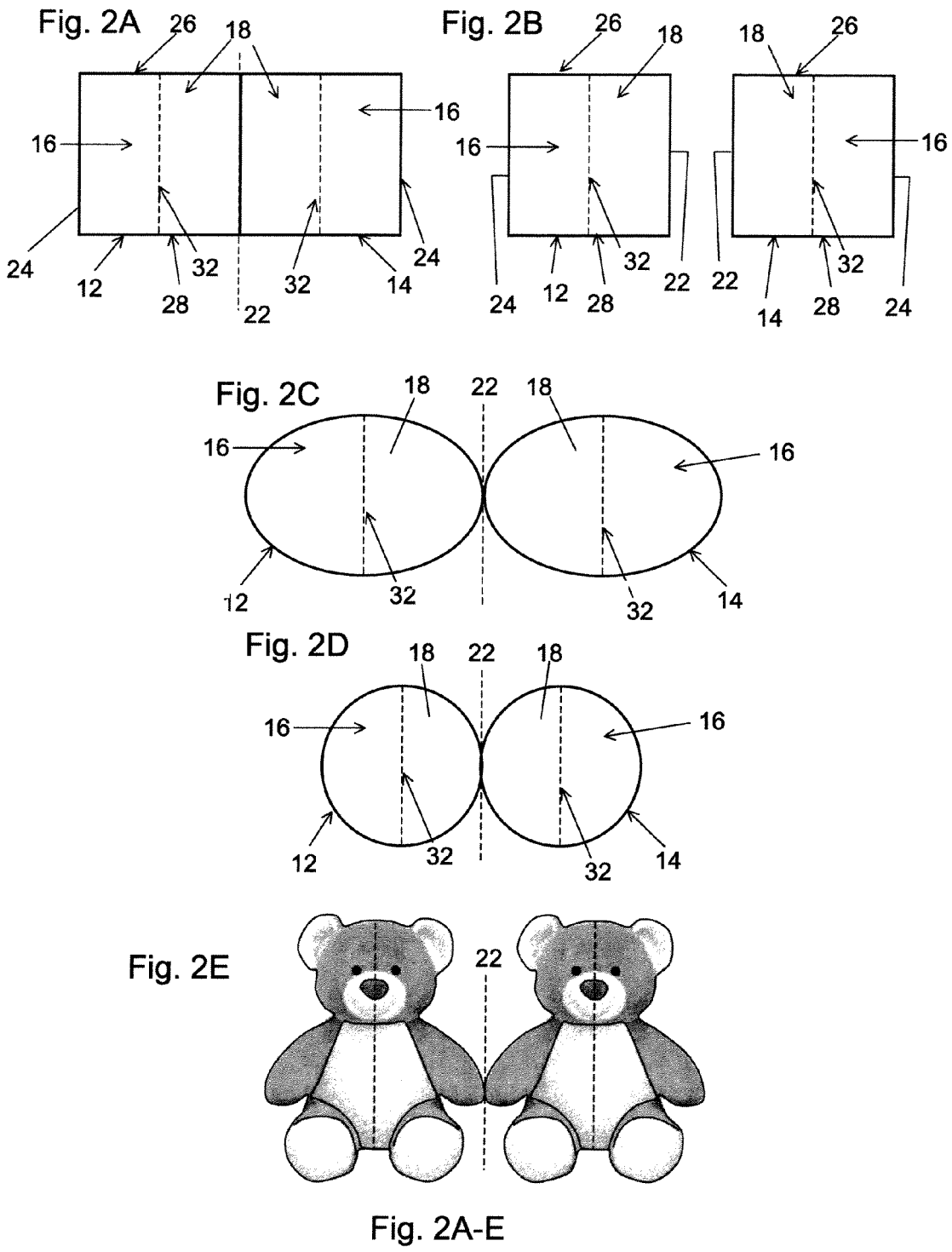
Fig. 2A-E

MINIATURE DENTAL FLOSSING PACKET

BACKGROUND OF THE INVENTION

1. Field of the Invention

The current invention relates generally to dental hygiene products, and more particularly to dental floss and applicators therefor. In particular, the current invention concerns a miniature dental flossing packet suitable for single use unobtrusive flossing. The packet comprises a length of dental floss comprising a flossing fiber, string, thread, strand or filament material, attached to and bundled or folded within two sheets of a flossing material holder, wherein said holder comprises two portions easily separable from each other and wherein two ends of said flossing material are unremovably attached to each of the two portions. Two portions of the flossing material holder are separated with a perforation along a line extending between the attachment points, enabling separation and tearing apart of the two portions by a simple pull on each portion, thereby extending said flossing material to its full length for easy and unobtrusive flossing. Both the flossing material and flossing material holder are made of a biologically acceptable, biodegradable and preferably digestible material.

2. Background and Related Disclosures

Dental floss, dental floss containers and flossing devices are known in the art and, typically, they are provided in large packaging for multiple uses in the privacy of a home or bathroom. However, in many social situations, the use of these flossing devices is not socially acceptable and would be embarrassing to a user. Consequently there is a need for an unobtrusive single use flossing means.

Additionally, flossing is difficult for children and training children to floss and getting children to floss on a regular basis presents a substantial problem for parents.

The current invention provides a single use, unobtrusive miniature dental flossing packet suitable for use in a social setting without causing embarrassment to the user. The miniature dental flossing packet comprises a small holder for flossing material that can be easily held between a thumb and forefinger of each hand, and easily separated into two portions, thereby releasing the flossing material stored within into its full length. The length of the flossing material is such that it is sufficient to remove food from between the teeth while covering the mouth with both hands. Following the use, the packet containing used flossing material and the holder is rolled into a small easily disposable bundle or, when both the holder and the flossing material are made of edible material, the used packet can be swallowed.

It is therefore a primary object of this invention to provide a simple, inexpensive means for unobtrusive removal of food from between teeth without causing a socially unacceptable embarrassment to an adult user and the means for encouraging children's flossing and flossing training.

SUMMARY

One aspect of the current invention is a miniature flossing packet suitable for a single use unobtrusive flossing for adults or for use by children.

Another aspect of the current invention is a miniature dental flossing packet comprising a length of dental floss, a dental floss holder comprising of two sheets of material having the two ends of the length of dental floss attached therein at a pair of attachment points, the two sheets being separable along a line extending between the pair of attachment points into two separate portions that can be held, gripped or pulled as tabs by a user to utilize the dental floss that extends between the two separated tabs, wherein the line along which the dental floss holder is separable is perforated to facilitate tearing.

Still another aspect of the current invention is a miniature dental flossing packet wherein the dental floss holder has a square, rectangular, oval, tubular or circular shape for use by adults, or has a shape of a cartoon figure, animal, toy, star, football or any other shape, or wherein said square, rectangular, oval, tubular or circular holder is decorated with a design of a cartoon figure, animal, toy, star, ball or any other design that is attractive to children, for use by children.

Yet another aspect of the current invention is a miniature dental floss packet having dimensions of a floss holder from about 1.5 cm to about 3 cm in width and from about 1.5 cm to about 5 cm in length, and the dental floss length from about 3 to about 10 cm wherein the dental floss holder is made of a biodegradable and/or digestible paper, cellophane, foil, polymer or another biodegradable or digestible material and wherein the dental floss is a fiber, string, thread, strand or filament made of biodegradable or digestible material.

Another aspect of the current invention is a miniature flossing packet comprising a flossing material attached to and bundled or folded within two sheets of a flossing material holder wherein said holder comprises two portions easily separable from each other and wherein said flossing material is unremovably attached to each portion at a pair of attachment points.

Still another aspect of the current invention is a miniature flossing packet wherein two portions of a floss holder are separable by simple pull on each portion, thereby releasing the floss bundle and unfolding said floss to its full length for easy and unobtrusive flossing.

Still yet another aspect of the current invention is a miniature flossing packet wherein both the flossing material and flossing material holder are made of biologically acceptable, biodegradable and preferably digestible material wherein said material is the same or different.

Yet another aspect of the current invention is a single use unobtrusive miniature flossing packet suitable for use in a social setting without causing embarrassment to the user wherein the miniature flossing packet comprises a small size floss holder that can be easily held between a thumb and forefinger of each hand and separated into two portions, thereby releasing the flossing material stored within into its full length that is sufficient to remove food from between the teeth while covering the mouth with both hands, then gently rolling the holder and the flossing material into a small easily disposable bundle or, when both the holder and the flossing material are made of edible material, swallowing the flossing packet.

Still yet another aspect of the current invention is a use of a miniature flossing packet by children for flossing and for training purposes for flossing in children wherein said packet is manufactured in a shape of a cartoon figure, animal, toy, star, ball or any other shape that is attractive to children and wherein for safety reasons both the packet and the flossing materials are made of a biodegradable, digestible and edible material.

Still yet another aspect of the current invention is a method of forming, fabrication or manufacturing of a miniature dental floss packet, said method comprising steps:

a) providing a length of dental floss;
b) forming a dental floss comprising two sheets of material, said sheets facing each other and forming a pocket separable along a line extending between a pair of attachment points for a dental floss to two separate portions that can be gripped as tabs by a user to utilize the dental floss extending between the two tabs, wherein said two portions are separated by perforating said sheets along the line along which the sheets are separable to facilitate tearing;

c) attaching two ends of the dental floss to said two portions at the pair of attachment points; and d) joining a pair of substantially flat opposed sheets together along the edges after the two ends of the length of dental floss have been attached to one of the sides.

BRIEF DESCRIPTION OF FIGURES

FIG. 1A shows the miniature flossing packet in its finished form ready for use having a square shape. The rectangular shape would be an extended square shape seen in FIG. 1A in one dimension to form a rectangle. FIG. 1B shows an assembled oval shaped packet having two portions separated by a perforation. FIG. 1C shows an assembled circular shaped packet having two portions separated with a perforation. FIG. 1D shows a miniature flossing packet for use by children wherein the packet has a shape of a teddy bear character.

FIG. 2A shows a flossing holder material precut into a double square shape for fabrication of a miniature flossing packet in a square shape from one piece of the material. Two sheets forming front and back sides of the packet, two portions of each sheet and centered perforations are shown. FIG. 2B shows a precut double square material for fabrication of a miniature flossing packet in a square shape from two pieces of the material. The two sheets would be co-joined to form the packet. FIG. 2C shows a precut material for fabrication of a miniature flossing packet in an oval shape. FIG. 2D shows a precut material for fabrication of a miniature flossing packet in a circular shape.

FIG. 2E shows a precut material of fabrication of a miniature flossing packet in a teddy bear shape for use by children.

DEFINITIONS

Figure 1A:
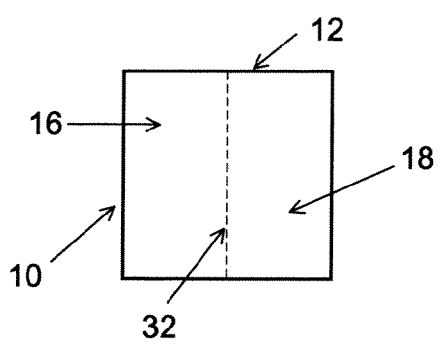
FIGS. 1A-1D show a miniature flossing packet having a square, rectangular, oval, circular or a cartoon shape before use wherein a flossing material holder is provided as a single structure showing a middle perforation that is easily separated into two parts by a pull.

As called herein, the term:

"Packet" means a small compact package or a pocket-like folder harboring a flossing material all assembled together for carrying or storing the flossing material. The packet may have different shape but has at least a size and shape that is separable into two portions wherein each portion can be comfortably held between the thumbs and forefingers of each hand.

"Flossing material", "floss" or "dental floss" means any suitable material that can be prepared as a fiber, string, thread, strand or filament for use as a dental floss. Dental floss is generally made out of a polymeric synthetic compound. Such compounds are typically biologically acceptable materials such as nylon, Teflon, polyamide, polyethylene, high density polyethylene, polytetrafluoroethylene, chitosan, alginate, silk or cotton, each able to be produced as a fiber, string, thread, strand or filament. For example, nylon is defined as a fiber-forming substance of a long-chain synthetic polyamide. A polyamide is a polymerizable compound characterized by more than one amide group. Teflon is the polymerized polytetrafluoroethylene. The flossing material is preferably biodegradable and/or digestible.

"Flossing material holder" means a pocket-like structure formed of two sheets of material, wherein each sheet is made up of two portions that may be easily separated into two parts. Typically the holder is made of paper, cellophane, foil, film, wafer, foam or a polymer sheet using a suitable thin material that can be easily folded into a two sided pocket enabling attachment and storage of a flossing material between the two sides and within said pocket. The material used for the flossing material holder is preferably biodegradable and/or digestible.

DETAILED DESCRIPTION OF THE INVENTION

The invention generally concerns dental hygiene products, and more particularly a dental floss and applicators therefor as a simple means for unobtrusive flossing for removal of food from between teeth in social settings without causing a socially unacceptable embarrassment to the user. Additionally the invention can be used safely for flossing by children and also for their training to floss and for encouraging them to floss.

Specifically, for use by adults, the invention concerns a miniature flossing packet that is inconspicuous, not undesirably noticeable or blatant, and is practical, convenient, easily storable, easily disposable and inexpensive. The packet can be carried in the purse, wallet or pocket or placed in a small container on a table, for example, in restaurants, hotel rooms, restrooms, or become a part of a travel or hygienic kits, etc.

For use by children, the packet can be made more attractive by being provided in the shape of a cartoon or toy character, or with a cartoon character or other attractive design printed or painted on another shape, in digestible form, and/or prepared from a flavored digestible materials thereby assuring its safety when digested by children. The miniature flossing packet is also useful as a training tool for children flossing and to encourage frequent flossing as children would be more apt to floss with a cartoon character or toy shaped packet releasing the flossing material.

I. A Miniature Dental Floss Packet

A miniature dental flossing packet provides a convenient, comfortable and hygienic means for an adult user for removal of food or food debris from between the teeth in social settings. It is small and inconspicuous, easily storable and usable and can be offered in restaurants, hotels, restrooms or carried in the purse, pocket, wallet or be a part of any hygienic kit for travel and instant use. For children's use, it can be used as an incentive for a child's flossing and/or for training small children to floss.

Figure 1B:
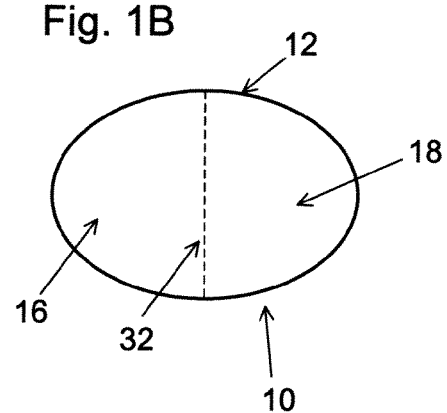
Figure 1C:
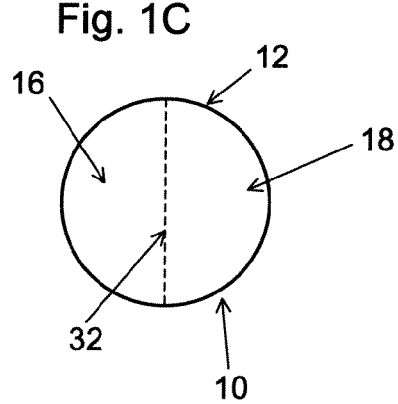
Figure 1D:
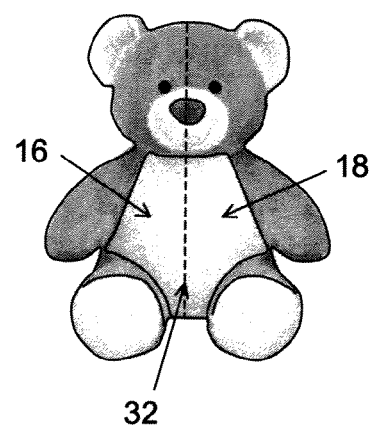

A miniature flossing packet of different shapes ready for use is shown in FIGS. 1A-1D. FIGS. 1A-1C show a side view of three representative shapes of the packet, namely a square, oval or circular packet 10 in their respective assembled form for use. A rectangular shape would be a sideways extended square shape. FIG. 1D shows a side view of a child's ready to use packet having a shape of a teddy bear, but could have a shape of any cartoon character, toy, animal, star, sports ball, or any other shape attractive to children. In addition, any of the shapes of FIGS. 1A-1C can be decorated with attractive designs, including any of the above listed shapes, or patterns or colors for use by adults or children.

The packet 10 is fabricated from two substantially flat and opposing sheets, the front sheet 12, seen in FIGS. 1A-1D, and the same size back sheet 14, seen in FIGS. 2A-2E, forming a front and back side of the packet. The two sheets have essentially the same size and shape and when assembled, form a pocket holding the floss. In FIGS. 1A-1D only the front sheet 12 is visible.

The sheets 12 and 14 are further each divided into two portions 16 and 18 separated by a perforation 32 centered along the axis 22. Thus each packet 10 can be held or gripped by the two portions 16 and 18 and easily separated and torn apart along the perforation 32 by pulling.

FIGS. 2A-2E show a precut sheet or sheets of holder material for fabrication of the miniature flossing packet. The precut may be one piece of material (FIGS. 2A and 2C-2E) that has the two opposed sides 12 and 14 connected at a common edge along the axis 22. Upon assembly, the two sides 12 and 14 are bent or folded over onto each other along an axis 22 that also forms a common edge 22. Alternatively, the packet 10 may be made of two separate sheets 12 and 14 (FIG. 2B) that are assembled together (after the flossing material is attached to each portion). As seen in FIGS. 2A-2E, the sheets or sides 12 and 14 are both perforated with centered perforation 32 such that, upon assembly, the perforation on both sides are joined in one perforation line for easy separation. The perforation 32 separates the sides 12 and 14 into two portions 16 and 18 that are, upon assembly, facing each other. The sheets 12 and 14 are co-joined and attached along their edges 22, 24, 26 and 28, for example, by gluing, pressing, adhesion, sealing or using any other chemical, physical or mechanical method, and form an internal pocket between sheets 12 and 14 for attachment and pre-use storage of the flossing material. FIGS. 2A-2B show the precut material for square packets. FIGS. 2C-2E show the precut material for oval, circular and teddy bear shaped packets.

Figure 3A:
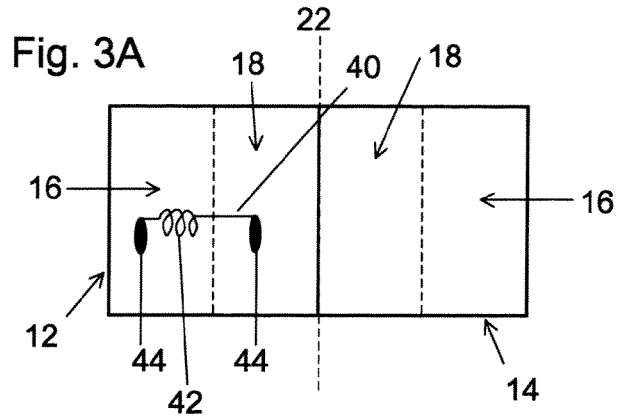
FIG. 3A shows a square shaped miniature flossing packet including the two sheets of the flossing material holder having attached flossing filament to one of the sheets before assembly into the packet. The filament is attached at a pair of attachment points to the two separable portions of one sheet with excess of the flossing material stored as a bundle or folded within the assembled packet.
Figure 3B:
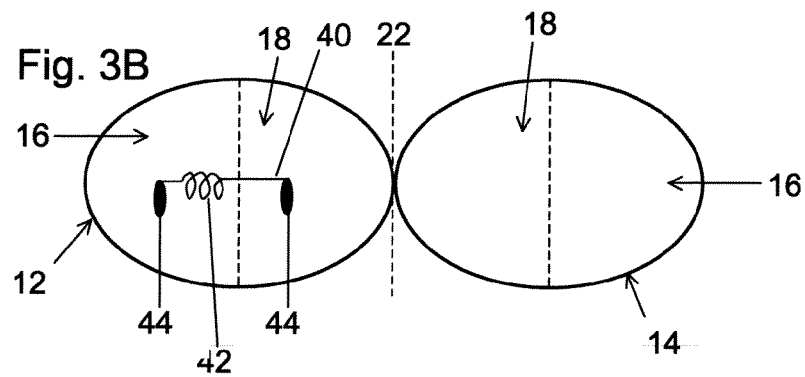
FIG. 3B shows an oval shaped miniature flossing packet having a flossing material attached to the two portions of one sheet, before assembly.
Figure 3C:
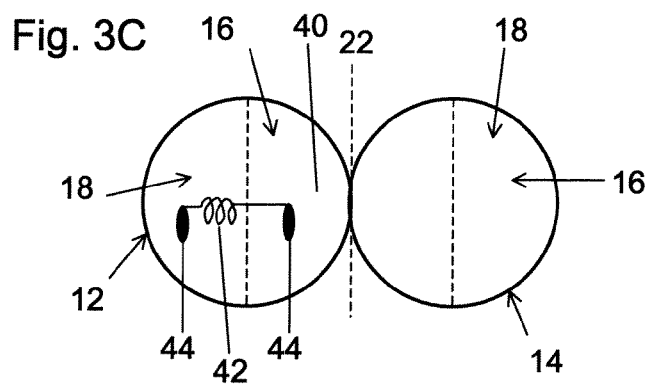
FIG. 3C shows a circular shaped miniature flossing packet having a flossing material attached to two portions of the holder, before assembly.
Figure 3D:
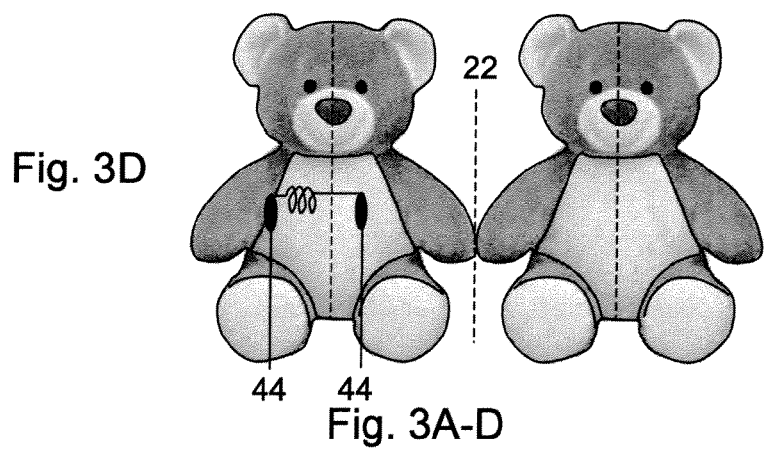
FIG. 3D shows a teddy bear shaped miniature flossing packet having a flossing material attached to two portions of the one sheet of the holder, i.e., to one teddy bear shape, before assembly. In all FIGS. 3A-3D, two sheets are folded upon assembly along an axis between the two sheets and co-joined, thereby forming the miniature dental flossing packet.

FIG. 3A shows an unassembled precut sheet defining the two sides 12 and 14 with a pair of attachment points sites 44 for attaching two ends of the flossing material 40 to the two sides of the packet. One end of the floss is attached at a attachment point 44 in portion 16 and the second end is attached at the attachment point 44 in portion 18, both on one side of sheet 12. One side of the sheet 12 wherein the floss is attached is then covered with the sheet 14 and co-joined thereby forming a pocket harboring the stored floss 40. The sheets 12 and 14 both have a perforation 32 that enables easy separation of the assembled packet 10 into two portions 16 and 18, each having one end of the floss attached thereto.

One end of flossing material 40 is thus attached to portion 16 and the other end is attached to portion 18 so that when the two portions are separated by tearing along the perforation 32, the floss material extends between portions 16 and 18 across the perforation 32.

In its storable assembled form, the flossing material is attached to sites 44 inside the pocket created by assembling sheets 12 and 14 into the packet 10 with the excess of the flossing material stored as a flossing material bundle 42. Since FIG. 3A shows an unassembled packet, the flossing material seems to be extended, however, in the assembled form for use, the flossing material will be stored as a bundle or folded between the two sides 12 and 14. In the assembled form seen in FIGS. 1A-1D, the flossing material is not visible since it would be stored inside of the pocket under the sheet 12 of the packet 10. In FIGS. 2A-2E the flossing material has not yet been attached.

Figure 4A:
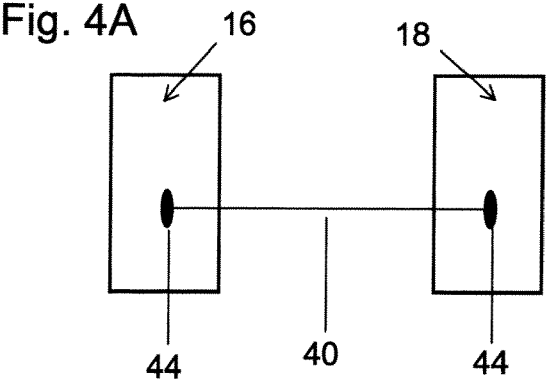
FIG. 4A shows a square shaped miniature flossing packet separated into two portions for its use, showing two portions of the holder with a flossing material extended to its full length between the separated portions.
Figure 4B:
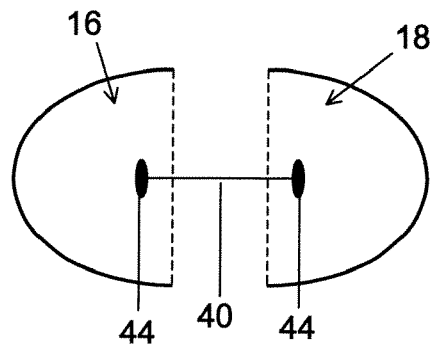
FIG. 4B shows an oval shaped miniature flossing packet in use.
Figure 4C:
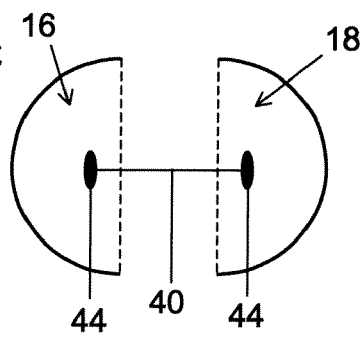
FIG. 4C shows a circular miniature flossing packet in use.
Figure 4D:
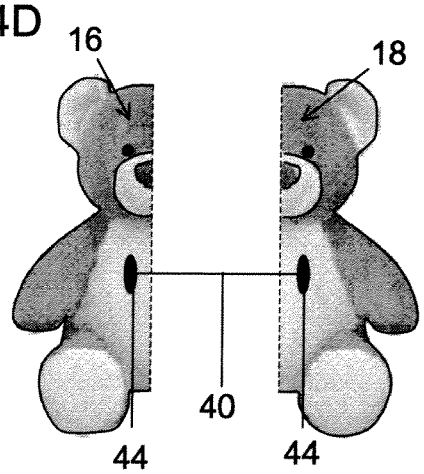
FIG. 4D shows a teddy bear shaped miniature flossing packet for use by children.

For use, the packet 10 is provided to the user, who holds the packet between the thumb and forefinger of each hand, pulls and tears the two portion 16 and 18 from each other thereby releasing the folded or bundled flossing material from its place between the two sheets of the packet. The packet separated into two portions for use is shown generally in FIG. 4. FIG. 4A shows a square packet separated into two portions wherein both ends of the flossing material remains attached to the portions 16 and 18 during the use, providing the user with about 3 to about 10 cm of flossing material that can be easily used while covering the mouth with both hands. The use of the miniature flossing packet thus provide the user with discreet means for flossing without exposing the flossing material.

Due to its miniature size and shape, the packet can be easily disposed of by simply rolling it into a small bundle or swallowing it if the material is digestible.

The miniature packet can be conveniently packaged for hygienic use in the paper cover that may be esthetically ornamental for placement on the table in restaurants, homes, hotel rooms, restrooms or carried in the purse, wallet, pocket or in a travel or hygienic kit.

II. Fabrication of a Miniature Dental Floss Packet

A miniature dental floss packet is fabricated using a method of the invention. The method basically comprises of several process steps, consisting of selecting suitable materials for both the holder and the floss, preparing the floss holder, attaching the floss to the floss holder and assembling the miniature dental floss packet.

A. Flossing Material Holder

The flossing material holder may be made of a single material or two different materials processed or molded into a sheet. Such material may be a paper, cellophane, foil, film, foam polymer sheet or any other material that is thin, pliable, biodegradable and preferably digestible and edible. The material used for fabrication of the holder may be flavored or unflavored. Also, a surface of the dental floss holder may be decorated with any design to make it attractive to be placed on the table or it may be decorated with a cartoon figure, animal, toy, star, ball or any other design that is attractive to children.

The holder is typically prepared from a biodegradable and preferably edible materials that are suitable to be produced in flat form, such as laminar sheets, wafers, films or foams made of or containing edible grade cellulose or other food grade cellulosic material, triglyceride material, collagen, gelatin, polypropylene, proteins, starch or any other edible material as may be conveniently used for preparation of the holder, each alone or in combination. In alternative, the material may be a composite of an edible film, foam, wafer or laminate sheet further covered with another edible material.

The selected material is precut into a single sheet or two sheets having a size and shape of the holder, having, typically, a square, rectangular, circular, tubular or oval shape as illustrated generally in FIG. 2. In alternative, it may have a shape of a cartoon figure or a toy.

Typically, each sheet is perforated in the middle before the flossing material is attached or affixed thereto, as seen in FIG. 2 to permit easy separation of the two portions for use. However, such perforation may also be made after the floss is attached provided that the care is taken to preserve the integrity of the flossing material.

The flossing material is then attached to two portions of the packet as illustrated generally in FIG. 3 showing an unfolded two sheets 12 and 14, each having two portions 16 and 18. After each end of the flossing material is attached to the two portions of the holder, the two sheets are folded over each other thereby forming a pocket completely hiding, concealing and sheltering the bundled or folded flossing material.

The method thus comprises a) selection of a length of dental floss, b) forming a dental floss holder separable, along a line extending between the pair of attachment points for a floss, into two separate portions that can be gripped as tabs by a user to utilize the dental floss extending between the two tabs, wherein said two portions are separated by perforating said holder along the line along which the holder is separable to facilitate tearing, as described above, c) attaching two ends of the dental floss to said holder at a pair of attachment points, and d) joining a pair of substantially flat opposed sides of the two sheets together along the edges after the two ends of the length of dental floss have been attached to one of the sides.

B. Size of the Miniature Floss Holder

Size of the flossing material holder is such that is provides for comfortable use and yet is inconspicuous when used. Typically, the size of the holder, before use, is from about 1.5-3 cm in width and about 1.5-5 cm in length.

C. Flossing Material

Flossing material suitable for preparation of dental floss is any suitable material for use as a dental floss. Dental floss is generally made out of polymeric synthetic compounds. Such materials are typically biologically acceptable materials such as nylon, Teflon, polyamide, polyethylene, high density polyethylene, polytetrafluoroethylene, chitosan, alginate, silk or cotton, each able to be produced as a fiber, string, thread, strand or filament. For example, nylon is defined as a fiber-forming substance of a long-chain synthetic polyamide. A polyamide is a polymerizable compound characterized by more than one amide group. Teflon is the polymerized polytetrafluoroethylene. The flossing material is preferably biodegradable, digestible and/or edible.

D. Attachment of the Floss to the Holder

The flossing material can be attached to the holder material by mechanical, chemical, physical, electrical or any other means known in the art. Such means may be, for example, gluing, adhesion, pressing, sewing, stitching, chemical or physical attachment.

E. Length of the Flossing Material

The flossing material has a reasonable length to permit its use for easy and convenient food removal. The length cannot be too short as it must permit the floss manipulation but it also cannot be too long as it might become entangled, knotted, etc., that would defeat the purpose of the invention.

Consequently, the length of the floss is between about 3 to about 10 cm, preferably between 4 and 7 cm and most preferably about 5 to 6 cm. For use by children, the length of the floss is between 3 and 8 cm, preferably between 4 and 7 cm and most preferably about 5 cm, when unfolded for use.

III. Use of the Miniature Dental Floss Holder

The miniature dental floss packet is used in the manner described above. The user, typically, picks up the packet with thumbs and forefingers of both hands, pulls on two outer portions of the packet, tears the packet into two portions along the perforation, and pulls the two portion from each other thereby releasing the folded floss and uses it to remove the food from between the teeth with the floss hidden behind the users hands. After flossing, the user rolls the packet into a small bundle and discretely disposes of it. In case when both the holder and floss material is digestible, the user can swallow the used packet without any detrimental health and safety effects.

What is claimed is:

1. A miniature dental floss packet, comprising:
   a dental floss made of a polymeric synthetic compound selected from a group consisting of biologically acceptable nylon, Teflon, polyamide, polyethylene, high density polyethylene, polytetrafluoroethylene, chitosan, alginate, silk and cotton, fabricated as a fiber, string, thread, strand or filament having a length between 3 cm and 10 cm; and
   a dental floss holder comprising of two sheets of material, said sheets separable into two portions, each portion having one ends of the length of dental floss attached therein at a pair of attachment points, the holder being separable along a line extending between the pair of attachment points, wherein said separable portions can be held, gripped or pulled as tabs by a user to utilize the dental floss extending between the two portions,
   wherein the dental floss holder has a shape selected from square, rectangular, oval, tubular, circular or has a shape of a cartoon figure, animal, toy, star, ball or any other shape optionally decorated with a design of a cartoon figure, animal, toy, star, ball or any other design that is attractive to children;
   wherein said holder is made of a biodegradable digestible material fabricated into a laminar sheet, polymer sheet, wafer, film, foam, paper, cellophane, foil, or a composite thereof, said biodegradable digestible material selected from the group consisting of edible grade cellulose, food grade cellulosic material, edible triglyceride material, collagen and gelatin, each alone or in combination.

2. The dental floss packet of claim 1 wherein the line along which the dental floss holder is separable is perforated to facilitate tearing.

3. The dental floss packet of claim 1 wherein said biodegradable digestible material is flavored.

4. The dental floss packet of claim 1 wherein said dental floss has a length between 4 and 7 cm.

5. The dental floss packet of claim 1 wherein the holder is formed of a pair of substantially flat opposed sheets of biodegradable digestible material co-joined together along the edges.

6. The dental floss packet of claim 1 wherein the holder has dimension from about 1.5 cm to about 3 cm in width and from about 1.5 cm to about 5 cm in length, and wherein the length of the dental floss is from about 5 to about 6 cm.

7. A method of forming, fabrication and manufacturing a miniature dental floss packet, said method comprising steps:
   a) providing a biodegradable dental floss having a length from about 3 to about 10 cm, said floss made of a polymeric synthetic compound selected from a group consisting of biologically acceptable nylon, Teflon, polyamide, polyethylene, high density polyethylene, polytetrafluoroethylene, chitosan, alginate, silk and cotton, fabricated as a fiber, string, thread, strand or filament;
   b) assembling a dental floss holder by joining two sheets of material in a square, rectangular, oval, circular or tubular shape, or having a shape of a cartoon character or toy, said two sheets separable into two portions, said portions having two ends of the length of the dental floss attached therein at a pair of attachment points wherein said holder is separable along a line extending between said pair of attachment points, wherein said separable portions can be held, gripped or pulled as tabs by a user to deploy the dental floss by extending said floss between said two separated portions, wherein said holder is made of a biodegradable digestible material fabricated into a laminar sheet, polymer sheet, wafer, film, foam, paper, cellophane, foil, or a composite thereof, said biodegradable digestible material selected from the group consisting of edible grade cellulose, food grade cellulosic material, edible triglyceride material, collagen, gelatin, each alone or in combination;

c) co-joining said two sheets of said biodegradable digestible material along the axis thereby forming a pocket for storing said attached dental floss; and d) sealing said co-joined sheets along the edges to form a miniature dental flossing packet.

8. The method of claim 7 further comprising a step of perforating said two portions of said holder along a line extending between said pair of attachment points thereby providing means to facilitate separation of said two portion from each other.

9. The method of claim 7 wherein the holder is formed of a single precut having the two opposed sheets connected at a common edge, said sheets folded along the common edge for co-joining and assembling the packet.

10. The method of claim 7 wherein the holder is formed of two separate precut sheets that are brought into contact together for co-joining and assembling the packet.

11. The method of claim 7 wherein the dental floss holder has square or rectangular shape.

12. The method of claim 7 wherein said dental floss holder is decorated with a design of a cartoon figure, animal, toy, star, ball or any other design that is attractive to children.

13. The method of claim 7 wherein said holder or said dental floss, or both are made of a flavored digestible material.

* * * * *